United States Patent [19]

Bennett, deceased

[11] Patent Number: Plant 7,187

[45] Date of Patent: Mar. 13, 1990

[54] MINIATURE ROSE PLANT NAMED 'ALWAYS A LADY'

[76] Inventor: Cecilia L. D. Bennett, deceased, late of 489 Minot Ave., Chula Vista, Calif. 92010, by Susan Mae O'Brien, executrix

[21] Appl. No.: 293,171

[22] Filed: Jan. 3, 1989

[51] Int. Cl.[4] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant, named 'Always A Lady', which is characterized by its soft mauve blooms, ranging from Amaranth Rose to Roseine Purple. The blooms are usually borne one to a stem with hybrid tea form but on occasion may be produced in sprays of 3 to 5 or more. The bush is vigorous, well-branched and produces moderate to heavy quantity of blooms.

1 Drawing Sheet

The present invention relates to a new and distinct variety of a hardy, dwarf, bush plant of the miniature class; the variety being primarily characterized as mauve.

The variety is further characterized by:

Long stemmed blooms of hybrid tea-type form, borne usually one to a stem but on occasion in sprays of 3 to 5 or more. The blooms are held very erect and well above the foliage.

It has a moderate damask fragrance.

The plant ranges in height from 18 to 24 inches (45 to 60 cm). The canes are sturdy and erect with moderate branching and medium to heavy foliage covering. The plant is a moderate to heavy bloomer that does well either in the greenhouse or outdoors.

The plant has good growth habits, well-shaped and attractive, bearing numerous leaflets of average size. I have found this variety to be easily asexually reproduced from cuttings.

The seed parent was Deep Purple (U.S. Plant Pat. No. 4,672), and the pollen parent was Dilly Dilly (U.S. Plant Pat. No. 6,141). It differs from its seed parent in the following ways. It is a miniature rose in pale mauve, and Deep Purple is a floribunda rose of deep mauve. It differs from its pollen parent in the following ways. It has 45 to 50 petals and an average diameter of 40 to 50 mm and is pale mauve, and Dilly Dilly has approximately 35 petals and an average diameter of 60 to 70 mm and is a deeper shade of mauve.

BRIEF DESCRIPTION OF THE DRAWING

The single color photographic view shows, in plan view, a bouquet of flowers of 'Always A Lady' in various stages of maturity from early bud stage to nearly full blown stage.

BOTANICAL DESCRIPTION

The descriptive matter which follows pertains to roses grown and color values observed in plants and newly opened blooms in the months of March through November 1988. The plants were grown outdoors in Chula Vista, Calif., and are believed to be accurate standards for this cultivar in similar conditions of soil and climate elsewhere.

Referring now specifically to the new and distinct variety of miniature rose plant named 'Always A Lady', the following is a detailed description thereof in outline; all major color plate identifications being by reference to the British Colour Counsel Horticultural Colour Chart, except where common terms of color definition are employed.

Type: Hardy, dwarf, bushy, greenhouse or outdoor, exhibition or garden decorative potted plant.

Class: Miniature.

Variety name: Always A Lady.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (35 to 50 mm); average diameter and sturdy; ranging from near Scheeles Green (860/3 to 860/1 page 175) to near Lettuce Green (861/3 to 861/1 page 176) with occasional tinting of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.*—Average for a miniature variety (40 to 50 mm).

*Petalage.*—Very double — 50 to 55 petals, arranged regularly, plus 5 to 10 petaloids.

*Form.*—Urn-shaped to ovoid as the bloom progresses. The petals remain somewhat cupped with the apex and/or margins reflexed outward, becoming at maturity more loosely cupped.

Petals: Fairly thick with good substance; both the upper and under surfaces of all petals have a matte finish.

*Shape.*—Outer Petals are of a broad obovate form with a slight peak at the apex. The intermediate petals are very much like the outer petals only narrower. The inner petals are a broad lanceolate form; and the petaloids are also lanceolate with some occasional irregularities.

Color: Newly opened flowers from plants grown outdoors (March through November of 1988), Chula Vista, Calif.:

*All petals.*—Upper and under surfaces — Ranging from near Amaranth Rose (530/3 to 530/1 page 139) to near Roseine Purple (629/1 to 629/2 page 150).

*General color effect.*—Newly opened flowers — Lavender throughout. Three days open — Little or no fading of color. Three to five days open — Some fading of color, but it remains pale mauve throughout the life of the bloom.

*Flower longevity.*—(March through November 1988) Plant in pot 3 to 5 days from bud with sepals reflexed to fully opened bloom. Holding at fully opened with only slight fading of color for 3 to 5 days longer. Cut bloom at living room temperature 5 to 7 days or longer.

Reproductive organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow in color.

*Ovaries.*—All encased in calyx.

*Hips.*—Some.

*Seeds.*—3 to 5 or more in each hip.

*Sepals.*—Permanent; spear-shaped; open as the bloom opens, recurving against the peduncle, when the bloom is fully opened.

Foliage:

*Leaves.*—Five to seven leaflets on the average; medium size for a miniature rose plant.

*Leaflets.*—Broad ovate-shaped.

*Margins.*—Very serrated with tinting of bronze, especially noticeable on the newer foliage.

*Color.*—Ranging from near Scheeles Green (860/2 to 860 page 175) to near Spinach Green (0960/2 to 0960/1 page 0960) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, bushy; average height for a miniature rose plant.

*Growth.*—Vigorous and well-branched.

*Canes.*—Medium diameter; sturdy; held erect.

*Main stems.*—Color range same as foliage.

*Thorns.*—Averaging less than 5 per 10 cm on the main stems and few if any on the branches. Reddish in color; small to average size; hooked slightly downward.

*Branches.*—Color range same as foliage.

The miniature rose plant and its flowers as herein described may vary in slight detail due to climate, soil and cultural conditions under which the variety may be grown; the present description being of the variety as grown in Chula Vista, Calif.

The following is claimed:

1. A new and distinct variety of miniature rose plant named, 'Always A Lady' of hardy, dwarf, vigorous growth, well-branched and attractive in appearance, substantially as illustrated and described, characterized by its hybrid tea-form blooms, ranging from near Amaranth Rose to near Roseine Purple, with flowers borne usually one to a stem but occasionally in sprays of 3 to 5 or more.

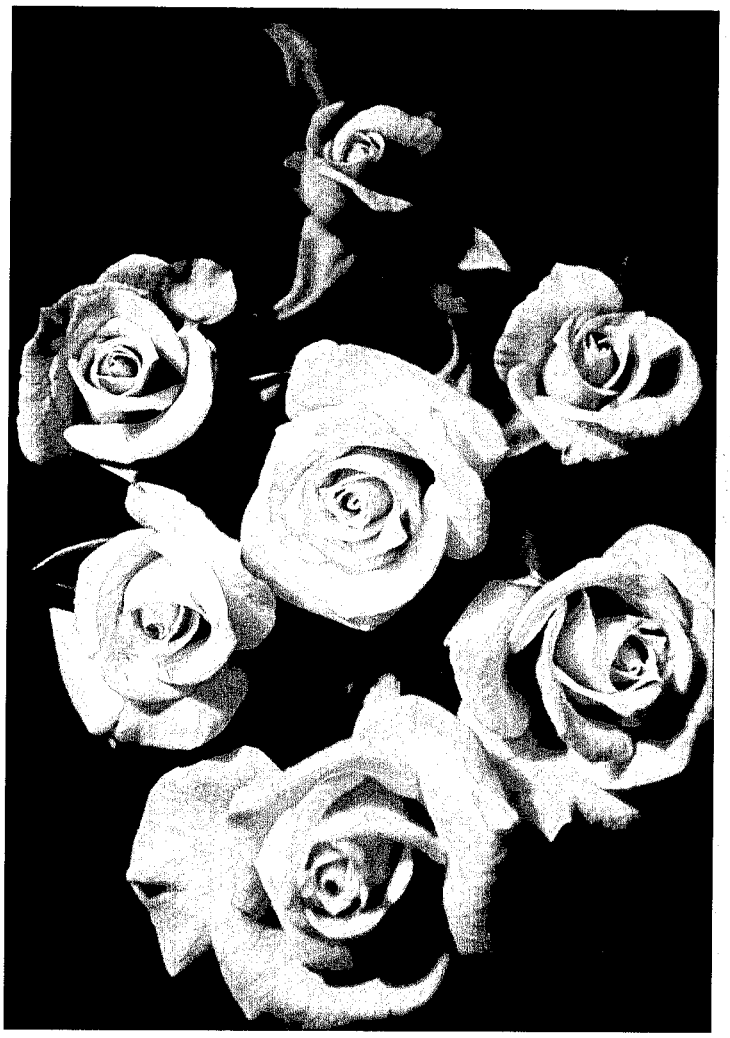

* * * * *